(12) United States Patent
Park et al.

(10) Patent No.: US 9,518,974 B2
(45) Date of Patent: Dec. 13, 2016

(54) SENSOR SYSTEM FOR DETECTING ORGANOPHOSPHORUS RESIDUES BY INDUCING COAGULATION OF GOLD NANOPARTICLES

(71) Applicant: CHUNG ANG UNIVERSITY INDUSTRY ACADEMIC COOPERATION FOUNDATION, Seoul (KR)

(72) Inventors: Tae Jung Park, Gimpo-si (KR); Myung-Sun Kim, Incheon (KR); Gi Wook Kim, Seoul (KR); Min Su Han, Seoul (KR)

(73) Assignee: CHUNG ANG UNIVERSITY INDUSTRY ACADEMIC COOPERATION, Seoul (KR)

( * ) Notice: Subject to any disclaimer, the term of this patent is extended or adjusted under 35 U.S.C. 154(b) by 0 days.

(21) Appl. No.: 14/707,972

(22) Filed: May 8, 2015

(65) Prior Publication Data

US 2015/0355154 A1    Dec. 10, 2015

(30) Foreign Application Priority Data

Jun. 10, 2014 (KR) ........................ 10-2014-0069980
Oct. 23, 2014 (KR) ........................ 10-2014-0144379

(51) Int. Cl.
| | | |
|---|---|---|
| *G01N 31/22* | (2006.01) | |
| *G01N 33/18* | (2006.01) | |
| *B82Y 15/00* | (2011.01) | |
| *G01N 21/80* | (2006.01) | |

(52) U.S. Cl.
CPC .......... *G01N 33/1826* (2013.01); *G01N 31/22* (2013.01); *B82Y 15/00* (2013.01); *G01N 21/80* (2013.01); *G01N 2033/184* (2013.01); *Y10S 977/773* (2013.01); *Y10S 977/921* (2013.01); *Y10T 436/163333* (2015.01)

(58) Field of Classification Search
CPC .... G01N 33/1826; G01N 33/18; G01N 33/00; G01N 21/82; G01N 21/77; G01N 21/75; G01N 2033/184
USPC ........ 436/104, 103; 977/772, 771, 766, 762; 422/430
See application file for complete search history.

(56) References Cited

U.S. PATENT DOCUMENTS

2011/0027869 A1* 2/2011 Hatton .................. A01N 25/24
                                                                435/262.5

FOREIGN PATENT DOCUMENTS

JP    2007-197435 A    8/2007

OTHER PUBLICATIONS

STN Search Report provided by STIC Services at USPTO, obtained on Apr. 20, 2016, pp. 1-72.*

(Continued)

*Primary Examiner* — Christine T Mui
(74) *Attorney, Agent, or Firm* — Knobbe Martens Olson & Bear LLP

(57) ABSTRACT

A sensor system detects organophosphorus pesticide residue by inducing the aggregation of gold nanoparticles. A method comprises aggregating gold nanoparticles by a reaction between an organophosphorus pesticide and imidazole or a green fluorescent protein (GFP), and detecting the organophosphorus pesticide based on a absorption spectral change resulting from the aggregation. The system for detecting pesticide residue is useful as a biosensor for analyzing pesticide residue in situ, because the optical change of the reagent by the presence of an organophosphorus pesticide is distinct, the detection speed is fast, and the range of detection limits is broad.

13 Claims, 13 Drawing Sheets

(56) References Cited

OTHER PUBLICATIONS

Shi, Huijie et al, Aptamer-based colorimetric sensing of acetamiprid in soil samples: Sensitivity, selectivity and mechanism, Journal of Hazardous Materials, 260, 2013, pp. 754-761.*

Lisha et al, Enhanced visual detection of pesticides using gold nanoparticles, Journal of Environmental Science and Health Part B, 44, 2009, pp. 697-705.*

Park et al., "A New Strategy for Detection of Organophosphorus Pesticides using Enhanced Green Fluorescent Protein and Aggregation-Induced Gold Nanoparticles", The 113th General Meeting of the Korean Chemical Society on Apr. 16, 2014 in 2 pages.

Park et al., "Biosensor composed of enhanced green fluorescent protein and gold nanoparticle for detection of organophosphorus pesticides", Biosensors 2014 on May 27, 2014.

Park et al., "Gold Nanoparticle-based optical biosensor for sensing of Organophosphorus pesticides", BioChip—A Road to the Creative Economy on Apr. 2, 2014.

Park et al., "Detection of organophosphorus pesticides using enhanced green fluorescent protein and gold nanoparticle", Biochip Convergence: A Marathon to Clinic on Nov. 13, 2013.

Al Simonian et al., "Nanoparticle-based optical biosensors for the direct detection of organophosphate chemical warfare agents and pesticides", Anal. Chim. Acta., (2005), pp. 69-77, vol. 534(1).

Vamvakaki et al. "Pesticide detection with a liposome-based nanobiosensor", Biosensors and Bioelectronics 22 (2007) pp. 2848-2853.

Korean Office Action dated Nov. 24, 2014 of corresponding Korean Patent Application No. 10-2014-0144379—6 pages.

Li, H., et al., "Visual detection of organophosphorus pesticides represented by mathamidophos using Au nanoparticles as colorimetric probe", Talanta, 2011, vol. 87, pp. 93-99.

Enami, Y., et al., "Detection of organophosphorus compound based on a sol-gel silica planar waveguide doped with a green fluorescent protein and an organophosphorus hydrolase", Applied Physics Letters, 2011, vol. 98, 233503.

Karami, R., et al., "Design of a Fluorimetric Nanobiosensor for Detection of Organophosphorus Compounds" Proceedings of the 4th International Conference on Nanostructures, 2012. pp. 744-746.

* cited by examiner

US 9,518,974 B2

SENSOR SYSTEM FOR DETECTING ORGANOPHOSPHORUS RESIDUES BY INDUCING COAGULATION OF GOLD NANOPARTICLES

TECHNICAL FIELD

The present disclosure relates to detecting organophosphorus pesticide residue.

BACKGROUND ART

Organophosphorus pesticides are agricultural chemicals that are most widely used and are marketed for the purpose of controlling pests. These organophosphorus pesticides are less persistent than organochlorine pesticides, and thus have a lower residual risk. In addition, these have strong pesticidal activity, but are highly toxic for humans and livestock, and need to be used in relatively large amounts because these have low persistence. Organophosphorus pesticides that are frequently used include diazinon, iprobenfos, edifenphos, dichlorovos, parathion, malathion, and EPN (o-ethyl-o-(p-nitrophenyl)-phenyl phosphothioate.

Residual pesticides that are low-molecular-weight toxic chemicals are concentrated in the body even in small amounts and show toxicity, and thus adversely affect human health and the ecosystem. For this reason, continuous analysis and environmental monitoring for detecting the presence of pesticides are required, and a system for performing such analysis and monitoring needs to be introduced.

However, the conventional analysis of residual pesticides is performed using instrumental analysis methods that require expensive systems and professional manpower and mostly require large amounts of time and money. For this reason, it is required to develop a biosensor system capable of detecting residual pesticides in situ in a convenient and rapid manner.

Conventional systems for detecting organophosphorus pesticide residue using AChE (acetylcholinesterase) or OPH (organophosphate hydrolase) have disadvantages in that expensive enzymes and complex experimental procedures are required, a plurality of sample solutions should be separately prepared, and reactions between enzymes and substrates are time-consuming.

For example, a nano-biosensor for detecting pesticides using liposomes (Vicky Vamvakaki et al., Biosens. Bioelectron., 22(12): 2848-2853, 2007) is based on the principle in which AChE hydrolyzes nano-sized liposome complexes to generate a fluorescence signal, and the intensity of the fluorescence is reduced due to the decrease in the degree of the hydrolysis when the activity of the enzyme is reduced by the pesticide, and this change in the fluorescence is measured. However, it has disadvantages in that a process for forming liposome complexes is complicated, and many kinds of reagents, including buffer, liquid nitrogen and 5,5'-dithiobis-nitro-benzoic acid (DTNB), are required.

In addition, an optical biosensor for detecting organophosphorus compounds using OPH (organophosphate hydrolase) and gold nanoparticles (A L Simonian et al., Anal. Chim. Acta., 534(1):69-77, 2005) is also based on a fluorescence detection method. In this method, OPH-gold nanoparticle conjugates are formed using ester, and when 7-hydroxy-9H-(1,3-dichloro-9,9-dimethylacridin-2-one) (DDAO) phosphate is added to the conjugates, the DDAO phosphate bind to the conjugates and shows fluorescence by the gold nanoparticles. In this case, when an organophosphorus pesticide is present, OPH binds to the pesticide while it becomes distant from the DDAO phosphate and gold nanoparticles, and thus the intensity of the fluorescence decreases. This change in the fluorescence is measured. However, this method has disadvantages in that the reagents and time for conjugating OPH to gold nanoparticles are required and the limit of detection is low.

Meanwhile, gold nanoparticles are nanomaterials that are most widely used in the biosensing field, and have various specific properties that do not appear in general organic materials. Thus, many sensor systems have been developed using gold nanoparticles. Gold nanoparticles have an extinction coefficient that is about $10^3$-$10^5$ higher than that of general organic dyes, and thus have a characteristic UV/Vis spectrum. Also, the intensity and sensitivity of the spectrum are high, and thus a change in color from red to blue according to the distance between gold nanoparticles occurs rapidly, and an invisible change in the color can be detected by measuring the spectrum.

The discussions in the foregoing background section is to provide general background information, and does not constitute an admission of the prior art.

SUMMARY

One aspect of the present invention provides a method of detecting an organophosphorus pesticide, the method comprising the steps of: (a) adding one or more solutions, selected from the group consisting of an imidazole solution, a histidine solution, a pyrazole solution, a histamine solution and a green fluorescent protein (GFP) solution, to a mixed solution of a pesticide-contaminated sample and gold nanoparticles to induce the aggregation of the gold nanoparticles; and (b) measuring absorbance, which results from the aggregation of the gold nanoparticles, at a wavelength of 600-700 nm.

Another aspect of the present invention also provides a method of quantifying an organophosphorus pesticide, the method comprising the steps of: (a) adding one or more solutions, selected from the group consisting of an imidazole solution, a histidine solution, a pyrazole solution, a histamine solution and a green fluorescent protein (GFP) solution, to a mixed solution of a pesticide-contaminated sample and gold nanoparticles to induce the aggregation of the gold nanoparticles; (b) measuring absorbance, which results from the aggregation of the gold nanoparticles, at a wavelength of 600-700 nm; and (c) quantifying the concentration of the pesticide based on the measured absorbance.

A further aspect of the present invention also provides a kit for detecting an organophosphorus pesticide, the kit comprising: a gold nanoparticle solution; and one or more solutions selected from the group consisting of an imidazole solution, a histidine solution, a pyrazole solution, a histamine solution and a green fluorescent protein (GFP) solution.

EMBODIMENTS

Figure 1:
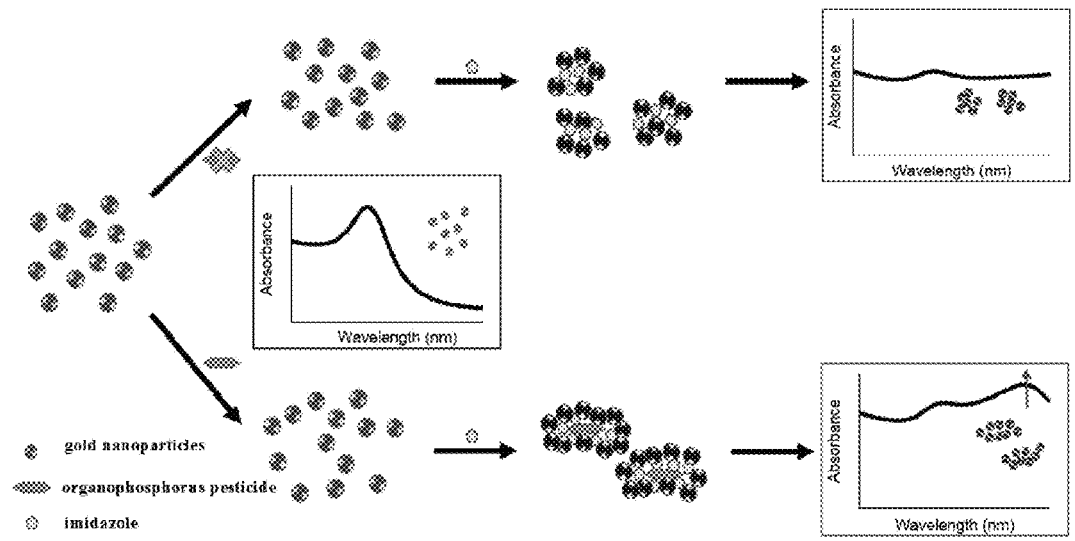
FIG. 1 shows changes in absorbance spectra, which occurred when a pesticide and imidazole were sequentially added to a gold nanoparticle solution.

Unless otherwise defined, all technical and scientific terms used herein have the same meaning as commonly understood by one of ordinary skill in the art to which the invention pertains. Generally, the nomenclature used herein are well known and commonly used in the art.

The present inventors have made extensive efforts, and as a result, have found that, when an organophosphorus pesticide is treated with the organic compound imidazole or a green fluorescent protein (GFP) instead of using an enzyme such as AChE or OPH, the aggregation size of gold nanoparticles will increase so that a great change will appear even in the presence of a low concentration of the pesticide, making it possible to detect even ppb levels of the pesticide.

In addition, the present inventors have paid attention to the property of gold nanoparticles that show a minute optical change according to the distance between the particles, and have made extensive efforts to enable a low concentration of an organophosphorus pesticide to be detected in a more rapid and easier manner. As a result, the present inventors have found that, when an imidazole solution is added to a solution containing an organophosphorus pesticide and gold nanoparticles, the gold nanoparticles will be aggregated by the added imidazole so that the absorption spectrum of the gold nanoparticles will change rapidly to enable the presence of the organophosphorus pesticide to be easily visibly recognized, thereby completing the present invention.

In embodiments of the present invention, a change in the absorbance spectrum of gold nanoparticles was measured using a spectrophotometer after adding a gold nanoparticle solution and an imidazole solution or a GFP solution to an organophosphorus pesticide. As a result, it could be seen that the aggregation of gold nanoparticles was induced by the organophosphorus pesticide and imidazole or GFP to produce a new spectrum showing the strongest peak at 600-700 nm, suggesting that the organophosphorus pesticide can be easily and rapidly detected based on a visible change in the spectrum.

Thus, one aspect of the present invention is directed to a method of detecting an organophosphorus pesticide, the method comprising the steps of: (a) adding one or more solutions, selected from the group consisting of an imidazole solution, a histidine solution, a pyrazole solution, a histamine solution and a green fluorescent protein (GFP) solution, to a mixed solution of a pesticide-contaminated sample and gold nanoparticles to induce the aggregation of the gold nanoparticles; and (b) measuring absorbance, which results from the aggregation of the gold nanoparticles, at a wavelength of 600-700 nm.

As used herein, the term "pesticide-contaminated sample" means a sample collected from crops suspected of contamination with a residual pesticide.

In an embodiment of the present invention, gold nanoparticles can be synthesized by reducing gold (III) chloride hydrate with citric acid. Processes of preparing gold nanoparticles in a liquid state include a process of reducing a metal salt at high temperatures without using a template, and a process of synthesizing gold nanoparticles using a template at room temperature.

In the process that does not use the template, metal nanoparticles are prepared by boiling a metal salt in a solvent, and then adding a strong reducing agent such as citrate at a temperature higher than the boiling temperature under a strong stirring condition. In another process, a surface stabilizer or a template may be used in order to overcome a thermodynamically unstable state during the formation of gold nanoparticles. In some cases, a hard template, such as mesoporous alumina or silica or carbon nanotubes (CNTs), or a soft template such as a surfactant, may be used. Processes for preparing nanoparticles using a template include a seed-mediated crystal growth process that uses a seed and a growth solution, and a polyol process.

Gold nanoparticles are nanomaterials that are most widely used in the biosensing field. Gold nanoparticles have an extinction coefficient that is about $10^3$-$10^5$ higher than that of general organic dyes, and thus have a characteristic UV/Vis spectrum. Gold nanoparticles have a characteristic color under visible light, and are aggregated by a specific bond that occurs during the measurement of a specific sample, and this aggregation causes a change in the permittivity of the gold nanoparticle surface, and as a result, the local surface plasmon condition changes, and thus the color of the gold nanoparticle solution changes under visible light. In other words, the red shift of the light absorption wavelength of gold nanoparticles occurs while the distance between the nanoparticles becomes closer, and the original red gradually changes to blue as a reaction between the gold nanoparticles and a sample progresses.

The present inventors have attempted to develop a colorimetric sensor enabling a sample to be visibly measured based on the color change of a solution itself, which occurs when there is a specific reaction between an organophosphorus pesticide, imidazole and gold nanoparticles, without using a particular analysis system.

Gold nanoparticles are characterized in that they have the strongest peak at 519 nm when the UV/Vis spectrum thereof is measured. However, it has been found by measurement with a UV/Vis spectrophotometer that gold nanoparticles are aggregated as a result of a reaction between imidazole and a pesticide and that the spectrum thereof changes so as to have the strongest peak at a wavelength of 600-700 nm, preferably 670 nm.

GFP that is used in embodiments of the present invention is a green fluorescent protein, and may preferably be EGFP (enhanced green fluorescent protein) as described in an example of the present invention. EGFP is a kind of GFP fluorescent protein, and means an enhanced green fluorescent protein obtained by substituting 1 or 2 amino acids in GFP with other amino acid. It has the property of showing fluorescence stronger than that of general GFP.

In an example of the present invention, EGFP is obtained by inducing the expression of EGFP in *E. coli* transformed with the recombinant DNA of EGFP gene and purifying the expression product was used. The fluorescent protein reacting with the organophosphorus pesticide and the gold nanoparticles is necessarily not limited to GFP or EGFP, but may be replaced with various fluorescent proteins including a red fluorescent protein (RFP), a cyan fluorescent protein (CFP), a yellow fluorescent protein (YFP), a blue fluorescent protein (BFP), an enhanced green fluorescent protein (EGFP), an enhanced cyan fluorescent protein ECFP), an enhanced yellow fluorescent protein (EYFP), an enhanced red fluorescent protein (ERFP), and an enhanced blue fluorescent protein (EBFP).

Another aspect of the present invention is directed to a method of quantifying an organophosphorus pesticide, the method comprising the steps of: (a) adding one or more solutions, selected from the group consisting of an imidazole solution, a histidine solution, a pyrazole solution, a histamine solution and a green fluorescent protein (GFP) solution, to a mixed solution of a pesticide-contaminated sample and gold nanoparticles to induce the aggregation of the gold nanoparticles; (b) measuring absorbance, which results from the aggregation of the gold nanoparticles, at a wavelength of 600-700 nm; and (c) quantifying the concentration of the pesticide based on the measured absorbance.

Figure 4:
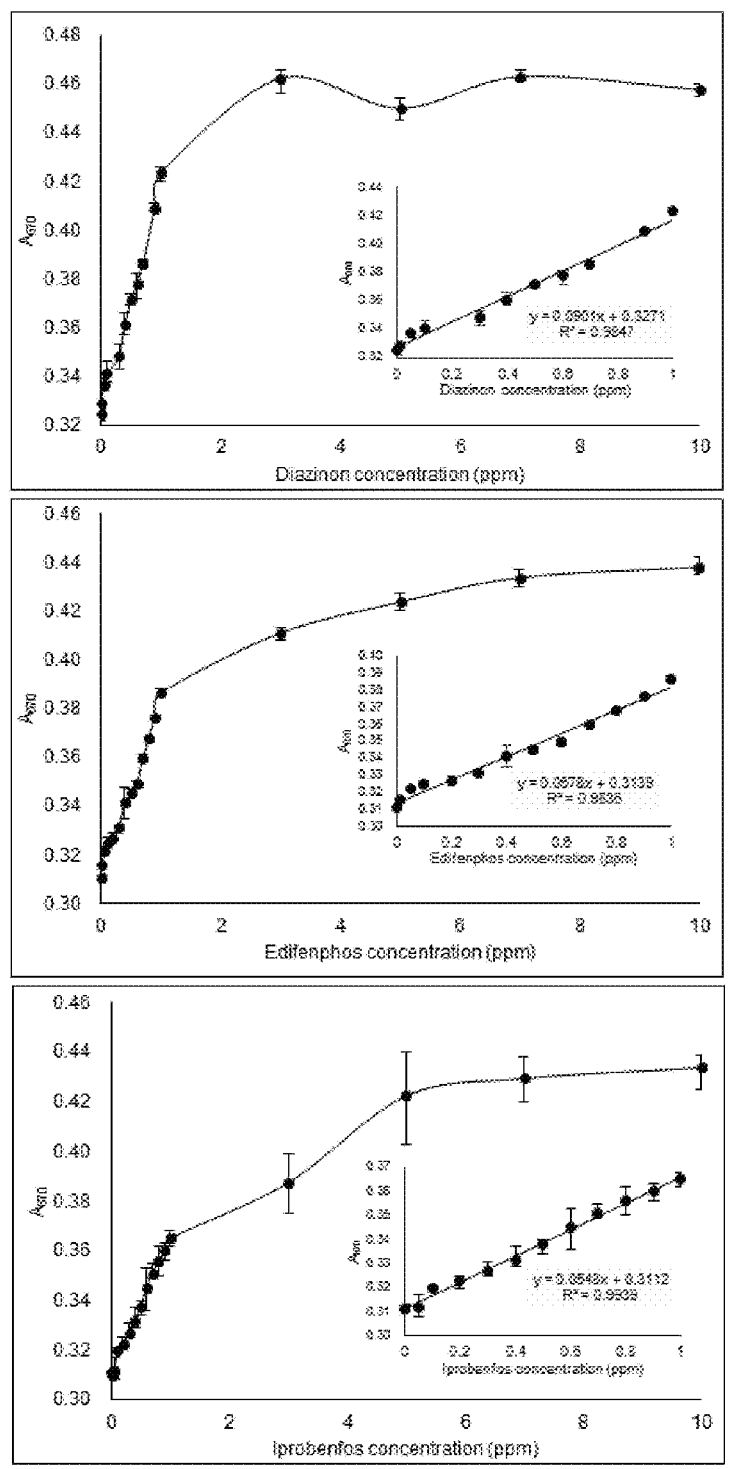
FIG. 4 is a set of standard curve graphs showing absorbance measured at 670 nm after adding gold nanoparticles and imidazole to varying concentrations of each of diazinon, edifenphos and iprobenfos.
Figure 14:
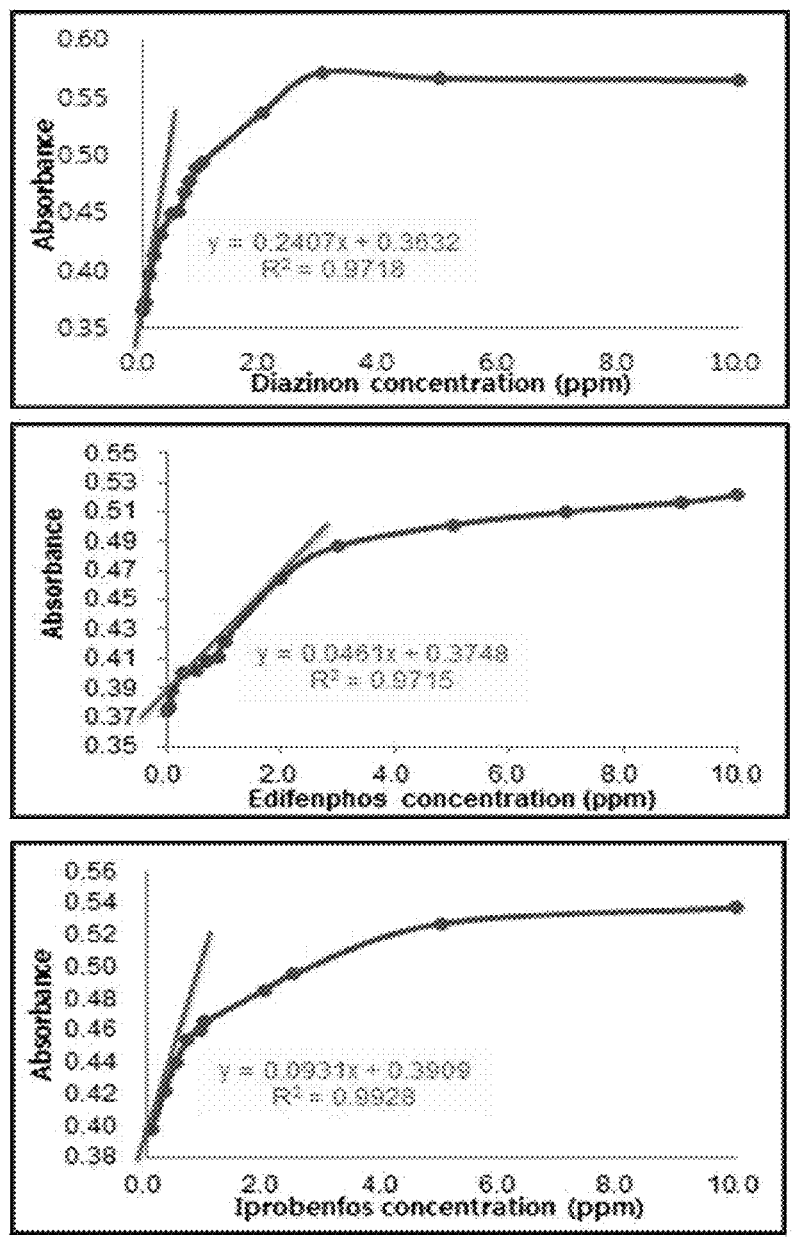
FIG. 14 is a set of standard curve graphs measured at 670 nm after adding gold nanoparticles and EGFP to varying concentrations of each of diazinon, edifenphos and iprobenfos.

In an example of the present invention, it could be seen that, when a gold nanoparticle solution and an imidazole solution or an EFGP solution were added to an organophosphorus pesticide, a great difference in absorbance between the concentrations of the pesticides appeared, and the difference was most clear at a wavelength of 670 nm. Thus, as shown in FIGS. 4 and 14, standard curves as a function of the concentration of the pesticide were plotted using the absorbance value at a wavelength of 670 nm. The minimum detection limit calculated using a 3-sigma method (calculated as three times the standard deviation of the mean values) was 27.9 ppb or 17 ppb, and the plateau appeared at a concentration of about 3 ppm, suggesting that the detectable range of the organophosphorus pesticide is 0.01-3 ppm.

In another example of the present invention, the results of quantifying an organophosphorus pesticide using embodiments of the present invention were compared with the results of quantifying an organophosphorus pesticide using HPLC (high-performance liquid chromatography). As a result, it could be seen that the method of quantifying a pesticide using gold nanoparticles and imidazole or GFP according to embodiments of the present invention is as accurate as HPLC and, at the same time, is more rapid and efficient than HPLC, suggesting that the method of embodiments of the present invention can substitute for the HPLC quantification method.

The specific concentration of a pesticide is calculated based on absorbance using the following equation: $A=\epsilon Lc$, wherein A is absorbance defined as $-\log(I/I_0)$. $I_0$ is the intensity of light before passage through a sample, and I is the intensity of light after passage through the sample. L is the distance by which light passed through a cuvette containing the sample, $\epsilon$ is the molar absorbity of the material, and c is the molar concentration of the sample. When L and $\epsilon$ are known, the concentration of the solute can be determined by measuring the absorbance (A) of the solution.

The method according to embodiments of the present invention may further comprise a pretreatment step of diluting the pesticide-contaminated sample in methanol, ethanol, or an aqueous solution thereof.

In an example of the present invention, a pretreatment process of dissolving an organophosphorus pesticide in 10% methanol was performed before the organophosphorus pesticide was allowed to react with gold nanoparticles and an imidazole solution or an EFGP solution. This pretreatment process is performed to extract an organophosphorus pesticide from a pesticide-contaminated sample. In place of methanol, ethanol that is a solvent having properties similar to those of methanol may be used, or an aqueous solution of methanol or ethanol may be used.

In embodiments of the present invention, the gold nanoparticles may have a diameter of 10-50 nm. When the size of the gold nanoparticles is 10-50 nm, the gold nanoparticles can show red so that the color shift phenomenon thereof can be most easily observed when the gold nanoparticles are aggregated due to an organophosphorus pesticide and imidazole.

In embodiments of the present invention, the organophosphorus pesticide may be diazinon, edifenphos or iprobenfos. The organophosphorus pesticide is a compound comprising a phosphorus (P) atom bonded to an alkyl or aryl group, and the detection method and quantification method according to embodiments of the present invention may also be applied to organophosphorus compounds such as dichlorovos, parathion, malathion, tebuconazole, acetamiprid, EPN, fenitrothion or fenthion.

In embodiments of the present invention, the concentration of the gold nanoparticle solution may be 8-12 nM, and the concentration of the imidazole solution may be 0.1-0.4 mM. Also, the detection concentration of the organophosphorus pesticide may be 0.01-3 ppm, and the optimum pH for the detection of the organophosphorus pesticide may be 7.4-8.9, and preferably 7.4-8.4.

In an example of the present invention, when a solution of 10 nM gold nanoparticle was mixed with a solution of 0.3 mM imidazole at a volume ratio of 1:1, the reaction of the mixture solution with the organophosphorus pesticide most easily occurred. Also, when the pH of the mixture solution was 8.4, a great difference in absorbance between the presence and absence of the organophosphorus pesticide appeared, suggesting that this pH is most suitable for the detection of organophosphorus pesticide.

Still another aspect of the present invention is directed to a kit for detecting an organophosphorus pesticide, the kit comprising: a gold nanoparticle solution; and one or more solutions selected from the group consisting of an imidazole solution, a histidine solution, a pyrazole solution, a histamine solution and a green fluorescent protein (GFP) solution.

In embodiments of the present invention, the concentration of the gold nanoparticle solution may be 8-12 nM, and the concentration of one or more solutions selected from the group consisting of an imidazole solution, a histidine solution, a pyrazole solution, a histamine solution and a GFP solution may be 0.1-0.4 mM.

EXAMPLES

Hereinafter, examples of the present invention will be described in further detail. It will be obvious to a person having ordinary skill in the art that these examples are illustrative purposes only and are not to be construed to limit the scope of the present invention. Thus, the substantial scope of the present invention will be defined by the appended claims and equivalents thereof.

Examples Using Gold Nanoparticles and Imidazole
Preparation of Sample and Instrument Trisodium citrate dehydrate used in the preparation of nanoparticles was purchased from BIO BASIC (CANADA INC.), and gold (III) chloride hydrate ($HAuCl_4$) was purchased from Sigma-Aldrich (USA). Gold nanoparticles were synthesized by reducing gold (III) chloride hydrate with citrate, and gold nanoparticles having a diameter of 13 nm were used in the following experiment.

Diazinon, edifenphos and iprobenfos, which are organophosphorus pesticides, and phosphate buffered saline (tablet) were purchased from Sigma-Aldrich (USA).

Methanol was purchased from Merck Chemicals, and imidazole was purchased from BIO BASIC (CANADA INC.), and Milli-Q grade water (18.2 MO/cm, Millipore) was used in all the experiments.

Absorbance was measured with a Synergy H1 Hybrid Reader purchased from Biotek (Korea).

Example 1

Measurement of the Change in Absorption Spectrum Caused by Adding Gold Nanoparticles and/or Imidazole to Organophosphorus Pesticides For diazinon that is an organophosphorus pesticide, 10 μl of the pesticide was dissolved in 10 mL of 10% methanol to a concentration of 1000 ppm. The solution was then diluted with 10% methanol to a concentration of 1 ppm to prepare a sample.

When gold nanoparticles and imidazole were added to the organophosphorus pesticide, a rapid change in the absorption spectrum (the shift of the peak) occurred. Thus, an experiment for examining an element that caused this change was performed.

1-1: Reaction of Diazinon with Gold Nanoparticle Solution

First, a solution obtained by diluting the organophosphorus pesticide diazinon to a concentration of 1 ppm was mixed with a solution of 10 nM gold nanoparticles at a volume ratio of 2:1, and the mixture was allowed to react at room temperature.

Figure 2:
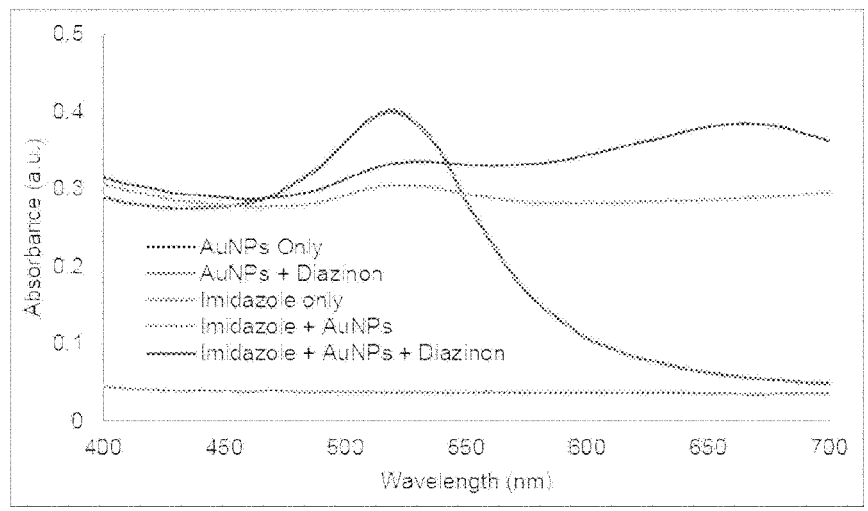
FIG. 2 is a graph showing changes in absorbance spectra, which were caused by specific components when gold nanoparticles and/or imidazole were added to an organophosphorus pesticide.

As a result, as shown in FIG. 2, the characteristic absorption spectrum of gold nanoparticles showed a peak at about 520 nm, and when the organophosphorus pesticide diazinon was reacted with gold nanoparticles, the peak position of the gold nanoparticles also appeared at 520 nm. Thus, it could be seen that diazinon alone did not directly influence the absorption spectrum of gold nanoparticles.

1-2: Reaction of Imidazole Solution with Gold Nanoparticle Solution

An organophosphorus pesticide was not used, and a solution of 0.3 mM imidazole was mixed with a solution of 10 nM gold nanoparticles at a volume ratio of 1:1, and the absorbance of the mixture was measured. As a result, as shown in FIG. 2, the shift of the peak was not observed, suggesting that imidazole alone cannot influence the absorption spectrum of gold nanoparticles.

1-3: Reaction of Mixture of Diazinon, Imidazole Solution and Gold Nanoparticle Solution A solution obtained by diluting the organophosphorus pesticide diazinon to a concentration of 1 ppm, a solution of 0.3 mM imidazole and a solution of 10 nM gold nanoparticles were mixed at a volume ratio of 2:1:1, and the mixture was allowed to react at room temperature, after which the absorption spectrum of the mixture was measured. As a result, as shown in FIG. 2, a new peak at 670 nm was produced. This suggests that the reaction of imidazole with the pesticide induces the aggregation of gold nanoparticles, which influences the absorption spectrum of the gold nanoparticles so as to make it possible to detect the organophosphorus pesticide.

For edifenphos, iprobenfos, malathion, tebuconazole, acetamiprid, fenitrothion and fenthion, the same experiment as described above was performed, and the same results could be obtained.

Example 2

Figure 3:
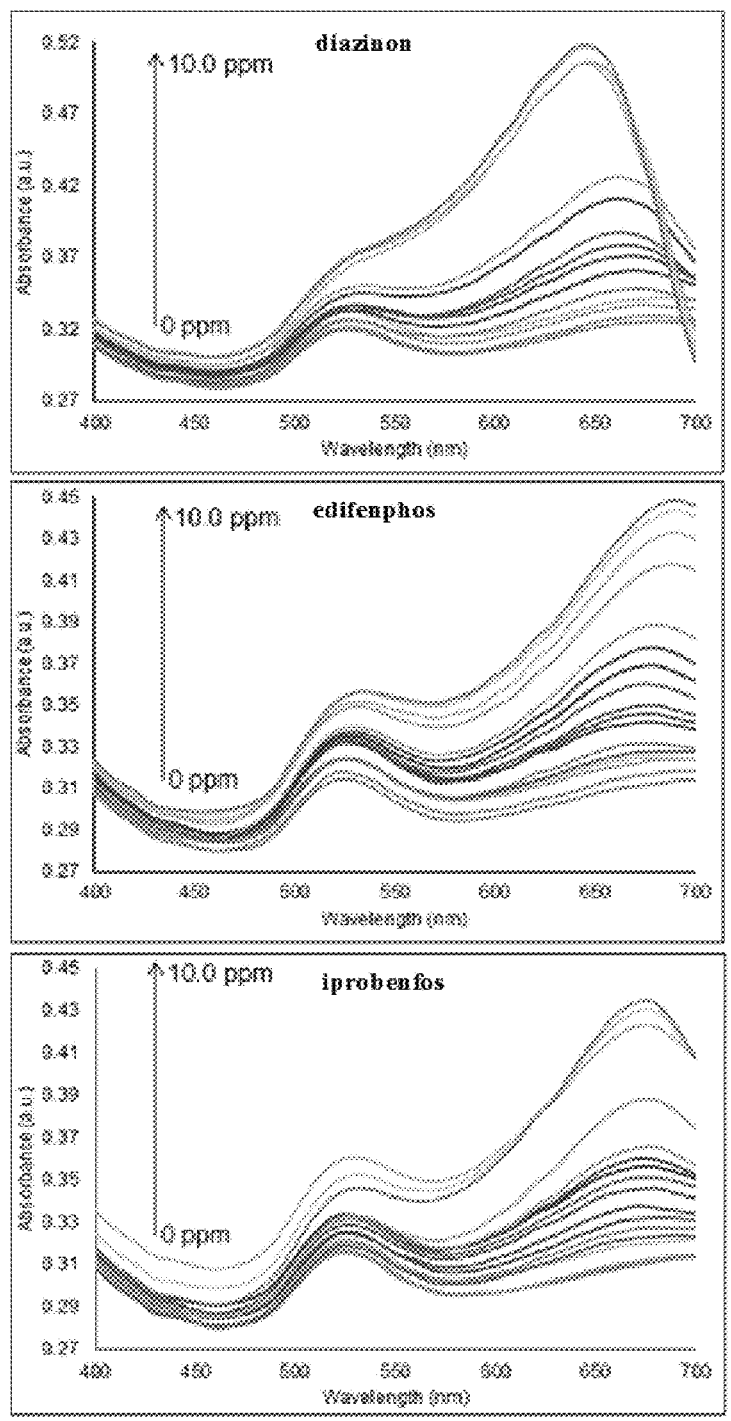
FIG. 3 is a set of graphs showing absorbance spectra obtained when gold nanoparticles and imidazole were added to varying concentrations of each of diazinon, edifenphos, iprobenfos, malathion, tebuconazole, acetamiprid, fenitrothion, and fenthion.

Measurement of Absorbance for Each of Organophosphorus Pesticides as a Function of Concentration For each of organophosphorus pesticides, including diazinon, edifenphos, iprobenfos, malathion, tebuconazole, acetamiprid, fenitrothion and fenthion, pesticide samples having various concentrations ranging from 0.01 ppm to 10.0 ppm were prepared. Then, each concentration of the organophosphorus pesticide sample, a solution of 10 nM gold nanoparticles and a solution of 0.3 mM imidazole were mixed at a volume ratio of 2:1:1, and a change in the absorption spectrum of each mixture was measured with a spectrophotometer at a wavelength of 400-700 nm (FIG. 3). Based on the results of the measurement, standard curves were obtained (FIG. 4).

As a result, as shown in FIG. 3, the position of the peak in the absorption spectrum was 670 nm and was the same between the concentrations of the pesticide, but a great difference in absorbance between the concentrations of the pesticide appeared, and this difference was most clear at a wavelength of 670 nm. Thus, as shown in FIG. 4, standard curves as a function of the concentration of the pesticide were plotted using the absorbance value at a wavelength of 670 nm. The minimum detection limit calculated using a 3-sigma method (calculated as three times the standard deviation of the mean values) was 27.9 ppb, and the plateau appeared at a concentration of about 3 ppm, suggesting that the detectable range of the organophosphorus pesticide is 0.01-3 ppm.

Comparative Example

Examination of Detection Specificity of Organophosphorus Pesticide Using Non-Pesticide Compound as Control In order to examine whether the pesticide detection sensor system comprising gold nanoparticles and imidazole shows a specific response only to an organophosphorus pesticide, a solution obtained by diluting each of benzene, phenol, toluene, xylene, dichlorobenzene and phosphoric acid, which are non-pesticide compounds composed of functional groups included in the formula of the organophosphorus pesticide, in 10% methanol to a concentration of 1 ppm, a solution of 10 nM gold nanoparticles, and a solution of 0.3 mM imidazole, were mixed at a volume ratio of 2:1:1.

Figure 5:
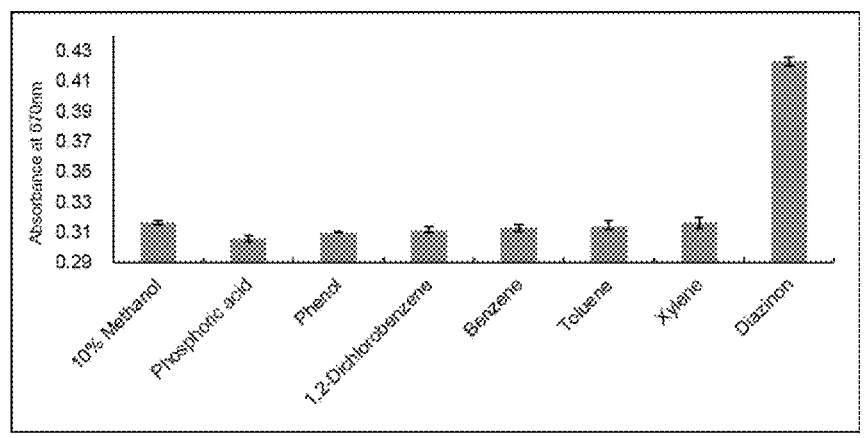
FIG. 5 is a graph showing absorbance measured at 670 nm after adding gold nanoparticles and imidazole to each of non-pesticide compounds and three organophosphorus pesticides.

The absorbance at 670 nm was analyzed. As a result, as shown in FIG. 5, the absorbance was significantly low (0.33 or lower) for benzene, phenol, toluene, xylene, dichlorobenzene, phosphoric acid and the like, which are non-pesticide compounds, and only the absorbance of the organophosphorus pesticide diazinon was as high as 0.41 or higher, suggesting that the sensor system showed a specific response to the organophosphorus pesticide.

Example 3

Figure 6:
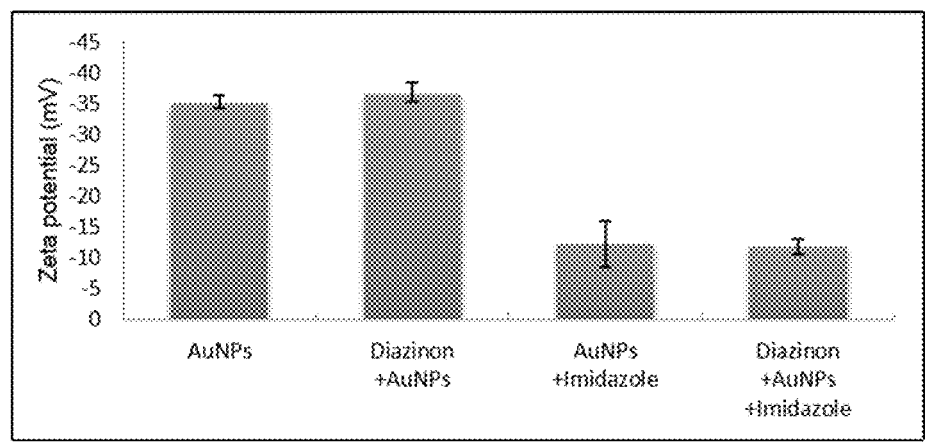
FIG. 6 is a graph showing changes in zeta potential, which occurred when gold nanoparticles and/or imidazole were added to an organophosphorus pesticide.

Change in Zeta Potential of Mixture of Organophosphorus Pesticide, Gold Nanoparticles and Imidazole An organophosphorus pesticide and an imidazole solution were sequentially added to a gold nanoparticle solution (the concentration and the mixing ratio were the same as described in Example 1-3), the zeta potential of the gold nanoparticles by the addition of each solution was measured with a zeta potential particle size analyzer. The zeta potential of the gold nanoparticles was −35 mV, and when the organophosphorus pesticide was added to the gold nanoparticles, the zeta potential was −36 mV, which did not substantially change. However, when imidazole was added to each sample, the zeta potential greatly increased to −12 mV, suggesting that imidazole greatly influences the aggregation of gold nanoparticle (FIG. 6), as described in Example 1-3.

Example 4

Change in Absorbance of Mixture of Organophosphorus Pesticide, Gold Nanoparticle and Imidazole as a Function of Time At a wavelength of 670 nm at which the change in absorbance was the greatest, the change in absorbance as a function of time was measured using varying concentrations of an organophosphorus pesticide in order to determine the most suitable reaction time. Absorbance was measured at intervals of 10 seconds for 40 minutes after an organophosphorus pesticide (0, 0.01, 0.1 and 1.0 ppm of diazinon), gold nanoparticles and imidazole were all added.

Figure 7:
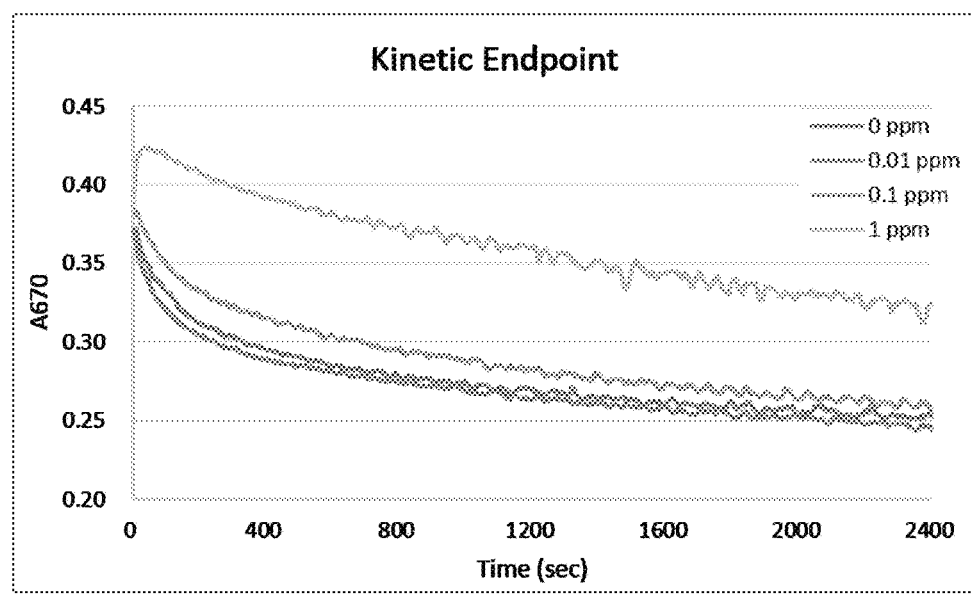
FIG. 7 is a graph showing the changes in absorbance of mixtures of varying concentrations of an organophosphorus pesticide, gold nanoparticles and imidazole, measured at 670 nm as a function of time.

As a result, as shown in FIG. 7, in the initial stage of the reaction, the change in absorbance was great, indicating that the reaction occurred rapidly. Thus, it was found that, when the reaction time was short, the greatest difference in the absorbance value between the concentrations of the pesticide well appeared. It can be seen that absorbance is measured within a very short reaction time, and thus the organophosphorus pesticide can be detected within a short time, and that the reaction occurs continuously over a long period of time.

Example 5

Change in Particle Size of Gold Nanoparticles

Figure 8:
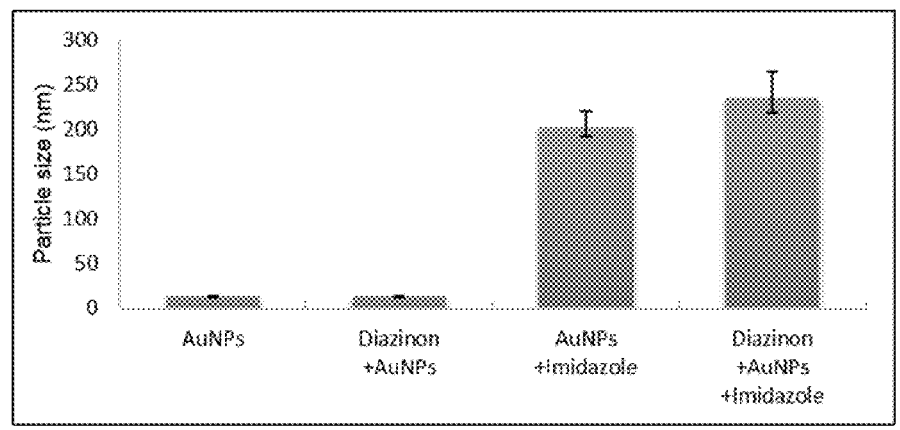
FIG. 8 is a graph showing the change in particle size caused by the aggregation of gold nanoparticles when gold nanoparticles and/or imidazole were added to an organophosphorus pesticide.

An organophosphorus pesticide and an imidazole solution were sequentially added to a gold nanoparticle solution (the concentration and the mixing ratio were the same as described in Example 1-3), the size of the gold nanoparticles by the addition of each of the pesticide and the imidazole solution was measured with a zeta potential particle size analyzer. The size of the gold nanoparticles was 13 nm, and when the organophosphorus pesticide was added to the gold nanoparticles, the particle size was 14 nm, which did not greatly change. However, when imidazole was added to the two samples, the particle sizes greatly increased to 202 nm and 235 nm, respectively, suggesting that imidazole greatly influences the aggregation of gold nanoparticles (FIG. 8), as described in Example 1-3.

Example 6

Change in Absorbance of Mixture of Organophosphorus Pesticide, Gold Nanoparticle and Imidazole as a Function of pH In order to examine whether the reaction of gold nanoparticles with an organophosphorus pesticide and imidazole is influenced by the pH of the solution, the change in the absorbance at 670 nm with a change in pH was analyzed (the concentration and the mixing ratio were the same as described in Example 1-3).

Figure 9:
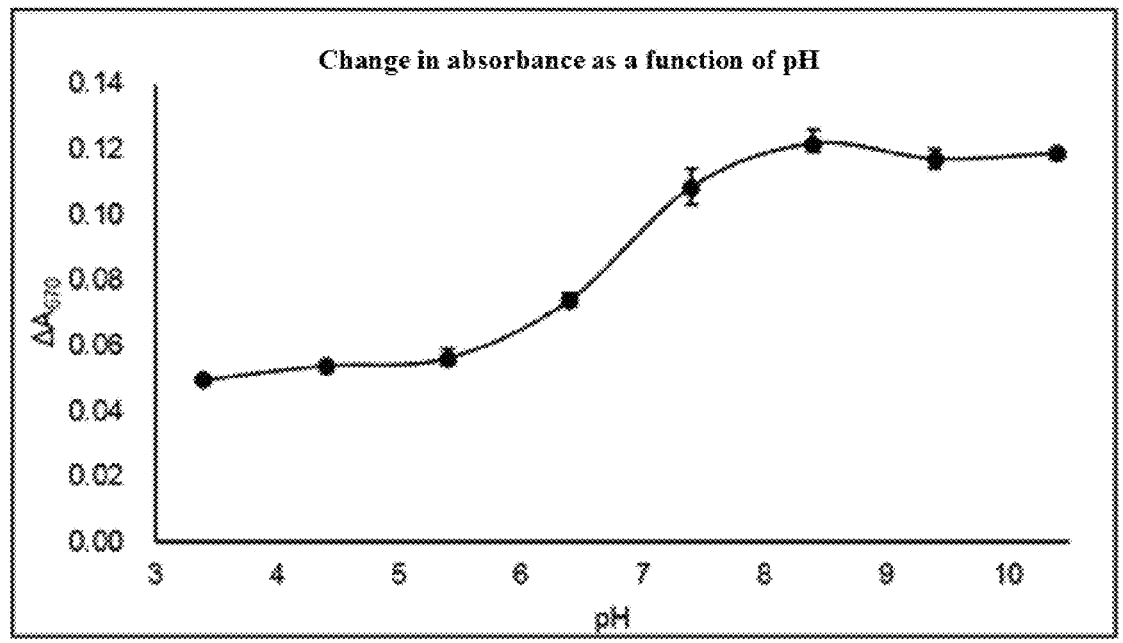
FIG. 9 is a graph showing a change in the absorbance of a mixture of an organophosphorus pesticide, gold nanoparticles and imidazole, measured at 670 nm as a function of pH.
Figure 10:
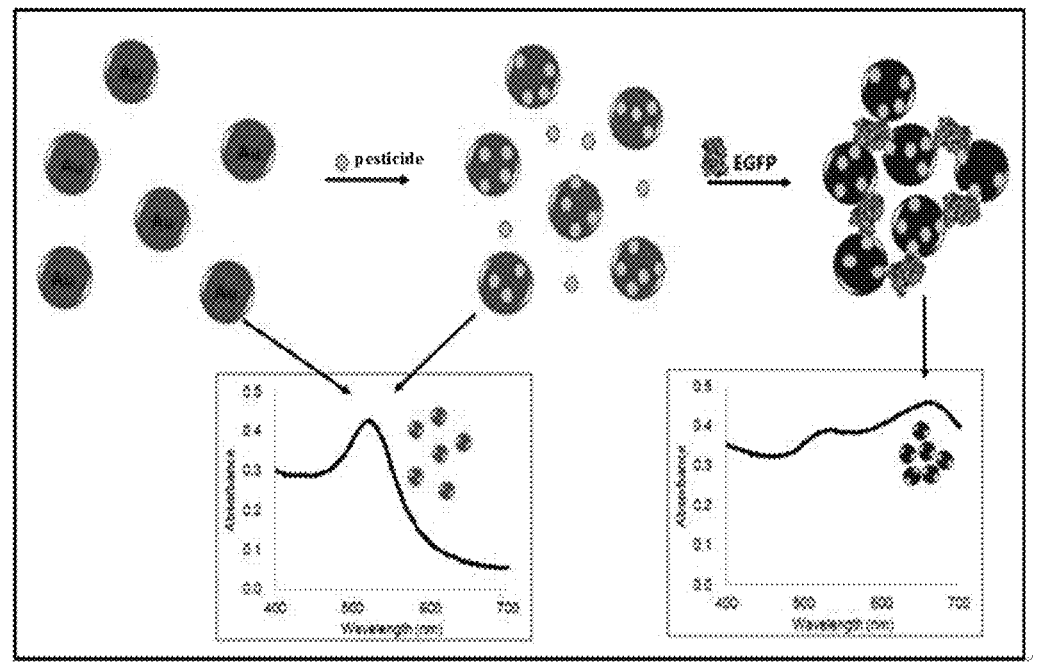
FIG. 10 shows changes in absorbance spectra, which occurred when a pesticide and EGFP were sequentially added to a gold nanoparticle solution.

Absorbance was analyzed at a pH ranging from 3.4 to 10.4. As a result, as shown in FIG. 9, the difference in the absorbance at 670 nm between 0 ppm and 1 ppm of the organophosphorus pesticide increased as the pH increased. The greatest difference appeared at pH 8.4.

Example 7

Comparison of the Results of Quantifying Organophosphorus Pesticide in Deionized Water and Tap Water Using Embodiments of the Present Invention with the Results of Quantifying Organophosphorus Pesticide Using HPLC The results of quantifying the concentration of an organophosphorus pesticide in deionized water and tap water by allowing gold nanoparticles to react with an organophosphorus pesticide and imidazole and then measuring the absorbance were compared with the quantification results obtained by HPLC (high-performance liquid chromatography) that is a general pesticide detection method, in order to demonstrate the accuracy of the inventive method of quantifying an organophosphorus pesticide (the concentrations of the gold nanoparticle solution and the imidazole solution and the mixing ratio were the same as described in Example 1-3).

The results of quantifying an organophosphorus pesticide in deionized water and tap water were compared with the results of quantifying an organophosphorus pesticide using HPLC.

TABLE 1

| | Samples | | |
|---|---|---|---|
| | 1 | 2 | 3 |
| Diazinon conc. Added (ppm) | 0.080 | 0.170 | 0.300 |
| In deionized water mean ± SD (ppm)* | 0.080 ± 0.024 | 0.173 ± 0.056 | 0.295 ± 0.042 |
| Recovery (%) | 100.4 | 101.6 | 98.3 |
| In tap water mean ± SD (ppm)* | 0.079 ± 0.012 | 0.146 ± 0.012 | 0.340 ± 0.001 |
| Recovery (%) | 98.5 | 86.3 | 113.5 |
| HPLC mean ± SD (ppm)* | 0.082 ± 0.002 | 0.149 ± 0.004 | 0.263 ± 0.064 |
| Recovery (%) | 96.2 | 87.6 | 87.7 |

*Mean value of three measurements; SD: standard deviation

As a result, as can be seen in Table 1 above, an organophosphorus pesticide was diluted to concentrations of 0.080 ppm, 0.170 ppm and 0.300 ppm, and then quantitatively analyzed using each of the method of embodiments of the present invention and HPLC. The results of the analysis were similar between the method of embodiments of the present invention and HPLC. The recovery obtained when using the quantification method of embodiments of the present invention was 100.1% in deionized water and 99.4% in tap water, which were higher than those obtained when using the HPLC quantification method (90.5%). Thus, it can be seen that the pesticide quantification method of embodiments of the present invention is as accurate as HPLC and, at the same time, is more rapid and efficient than HPLC, suggesting that the method of embodiments of the present invention can substitute for the HPLC quantification method.

Examples Using Gold Nanoparticles and GFP

Preparation of Sample and Instrument

Trisodium citrate dehydrate used in the preparation of nanoparticles was purchased from BIO BASIC (CANADA INC.), and gold (III) chloride hydrate (HAuCl$_4$) was purchased from Sigma-Aldrich (USA). Gold nanoparticles were synthesized by reducing gold (III) chloride hydrate with citrate, and gold nanoparticles having a diameter of 13 nm were used in the following experiment.

Diazinon, edifenphos and iprobenfos, which are organophosphorus pesticides, and phosphate buffered saline (tablet) were purchased from Sigma-Aldrich (USA).

Methanol was purchased from Merck Chemicals, and imidazole was purchased from BIO BASIC (CANADA INC.), and Milli-Q grade water (18.2 MO/cm, Millipore) was used in all the experiments.

EGFP used in the experiment was obtained by inducing the expression of EGFP in *E. coli* transformed with the recombinant DNA of EGFP gene and purifying the expression product.

Fluorescence and absorbance were measured with a Synergy H1 Hybrid Reader purchased from Biotek (Korea).

Example 8

Examination of Influence of Organophosphorus Pesticide on Activity of EGFP

For diazinon that is an organophosphorus pesticide, 10 μl of the pesticide was dissolved in 10 mL of 10% methanol to a concentration of 1000 ppm. The solution was then diluted with 10% methanol to concentrations of 10 ppb, 100 ppb, 1 ppm and 10 ppm to prepare samples.

In order to examine whether the intensity of fluorescence of EGFP is influenced by the organophosphorus pesticide, EGFP was added to each of the above-prepared pesticide samples having different pesticide concentrations, and each mixture was allowed to stand at room temperature for minutes. Then, using 10% methanol as a control, the intensity of fluorescence of the EGFP protein at each concentration was measured at an excitation wavelength of 480 nm and emission wavelength of 510 nm (FIG. 11).

Figure 11:
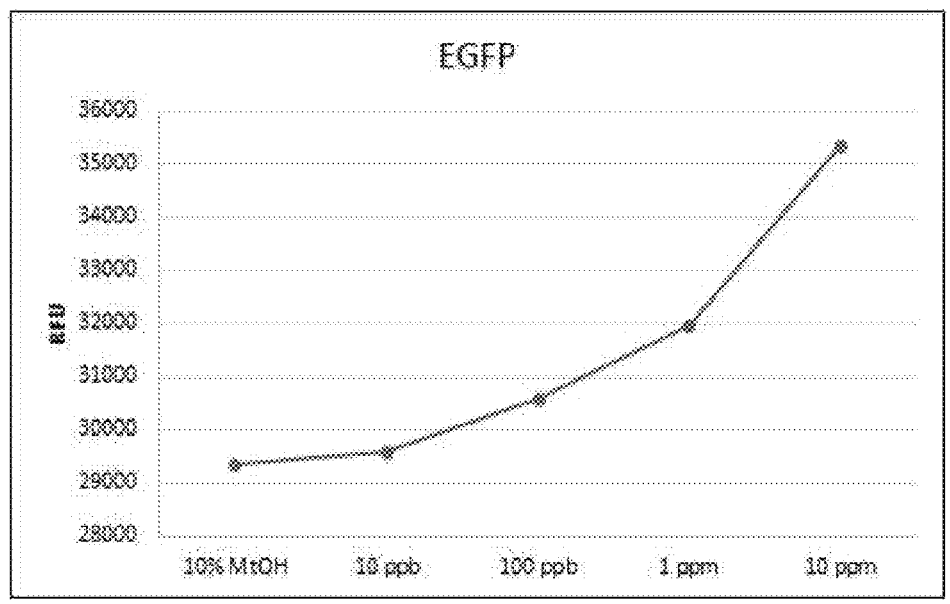
FIG. 11 is a graph showing the influence of an organophosphorus pesticide on the activity of EGFP.

As a result, as can be seen in FIG. 11, the intensity of fluorescence emitted from EGFP changed depending on the concentration of the pesticide. The intensity of the fluorescence increased as the concentration of the pesticide increased, and the intensity of the fluorescence increased rapidly at a concentration of 10 ppm.

For edifenphos and iprobenfos, the same experiment as described above was performed, and the same results could be obtained.

Example 9

Measurement of Absorption Spectral Change Caused by Adding Gold Nanoparticles and EGFP to Organophosphorus Pesticide When gold nanoparticles and imidazole were added to the organophosphorus pesticide, a rapid change in the absorption spectrum (the shift of the peak) occurred. Thus, an experiment for examining an element that caused this change was performed.

9-1: Reaction of Diazinon with Gold Nanoparticle Solution

First, a solution obtained by diluting the organophosphorus pesticide diazinon to a concentration of 1 ppm was mixed with a solution of 10 nM gold nanoparticles at a volume ratio of 2:1, and the mixture was allowed to react at room temperature.

Figure 12:
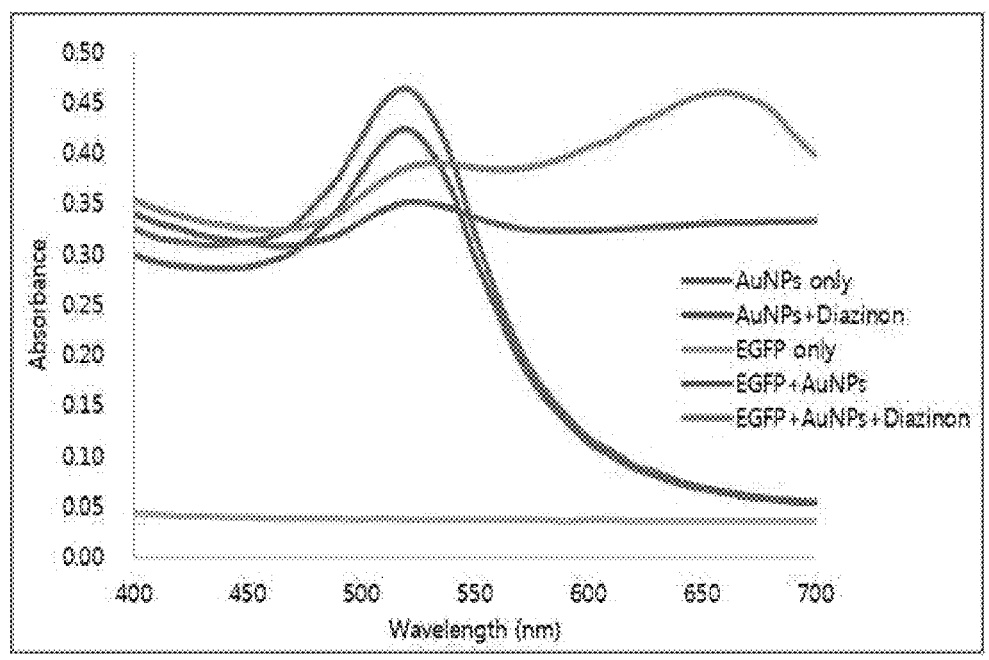
FIG. 12 is a graph showing any element that caused a change in absorbance when gold nanoparticles and/or EGFP were added to an organophosphorus pesticide.

As a result, as shown in FIG. 12, the characteristic absorption spectrum of gold nanoparticles showed a peak at about 520 nm, and when the organophosphorus pesticide diazinon was reacted with gold nanoparticles, the peak position of the gold nanoparticles also appeared at 520 nm. Thus, it could be seen that diazinon alone did not directly influence the absorption spectrum of gold nanoparticles.

9-2 Reaction of EGFP Solution with Gold Nanoparticle Solution

An organophosphorus pesticide was not used, and a solution of 5 μg/mL of EGFP was mixed with a solution of 10 nM gold nanoparticles at a volume ratio of 1:1, and the absorbance of the mixture was measured. As a result, as shown in FIG. 12, the shift of the peak was not observed, suggesting that EGFP alone cannot influence the absorption spectrum of gold nanoparticles.

9-3: Reaction of Mixture of Diazinon, EGFP Solution and Gold Nanoparticle Solution A solution obtained by diluting the organophosphorus pesticide diazinon to a concentration of 1 ppm, a solution of 5 μg/mL of EGFP and a solution of 10 nM gold nanoparticles were mixed at a volume ratio of 2:1:1, and the mixture was allowed to react at room temperature, after which the absorption spectrum of the mixture was measured. As a result, as shown in FIG. 12, a new peak at 670 nm was produced.

This suggests that the reaction of EGFP with the pesticide induces the aggregation of gold nanoparticles, which influences the absorption spectrum of the gold nanoparticles so as to make it possible to detect the organophosphorus pesticide.

Figure 13:
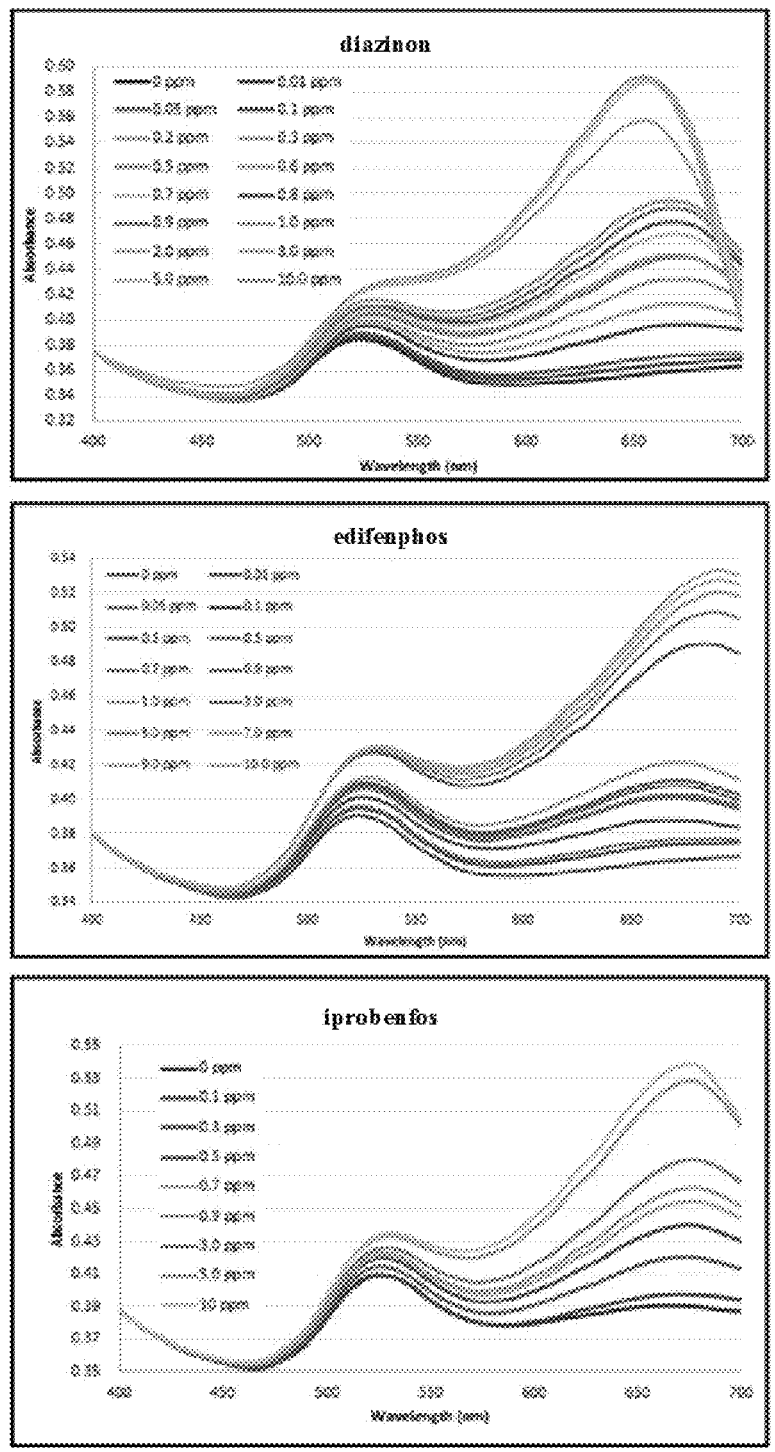
FIG. 13 is a set of graphs showing absorbance spectra measured after adding gold nanoparticles and EGFP to varying concentrations of each of diazinon, edifenphos and iprobenfos.

For edifenphos and iprobenfos, the same experiment as described above was performed, and the same results could be obtained (FIG. 13).

Example 10

Measurement of Absorbance for Each of Organophosphorus Pesticides as a Function of Concentration For each of organophosphorus pesticides, including diazinon, edifenphos and iprobenfos, pesticide samples having various concentrations ranging from 0.01 ppm to 10.0 ppm were prepared according to the method described in Example 8. Then, as described in Example 9, each concentration of the organophosphorus pesticide sample, a solution of 10 nM gold nanoparticles and a solution of 5 μg/mL of EGFP were mixed at a volume ratio of 2:1:1, and a change in the absorption spectrum of each mixture was measured with a spectrophotometer at a wavelength of 400-700 nm (FIG. 13). Based on the results of the measurement, standard curves were obtained (FIG. 14).

As a result, as shown in FIG. 13, the position of the peak in the absorption spectrum was 670 nm and was the same between the concentrations of the pesticide, but a great difference in absorbance between the concentrations of the pesticide appeared, and this difference was most clear at a wavelength of 670 nm. Thus, as shown in FIG. 14, standard curves as a function of the concentration of the pesticide were plotted using the absorbance value at a wavelength of 670 nm. The minimum detection limit calculated using a 3-sigma method (calculated as three times the standard deviation of the mean values) was 17 ppb, and the plateau appeared at a concentration of about 3 ppm, suggesting that the detectable range of the organophosphorus pesticide is 0.01-3 ppm.

Comparative Example

Examination of Detection Specificity of Organophosphorus Pesticide Using Non-Pesticide Compound as Control In order to examine whether the pesticide detection sensor system comprising gold nanoparticles and imidazole shows a specific response only to an organophosphorus pesticide, a solution obtained by diluting each of benzene, phenol, toluene, xylene, dichlorobenzene and phosphoric acid, which are non-pesticide compounds composed of functional groups included in the formula of the organophosphorus pesticide, in 10% methanol to a concentration of 1 ppm, a solution of 10 nM gold nanoparticles, and a solution of 5 μg/mL of EGFP, were mixed at a volume ratio of 2:1:1.

Figure 15:
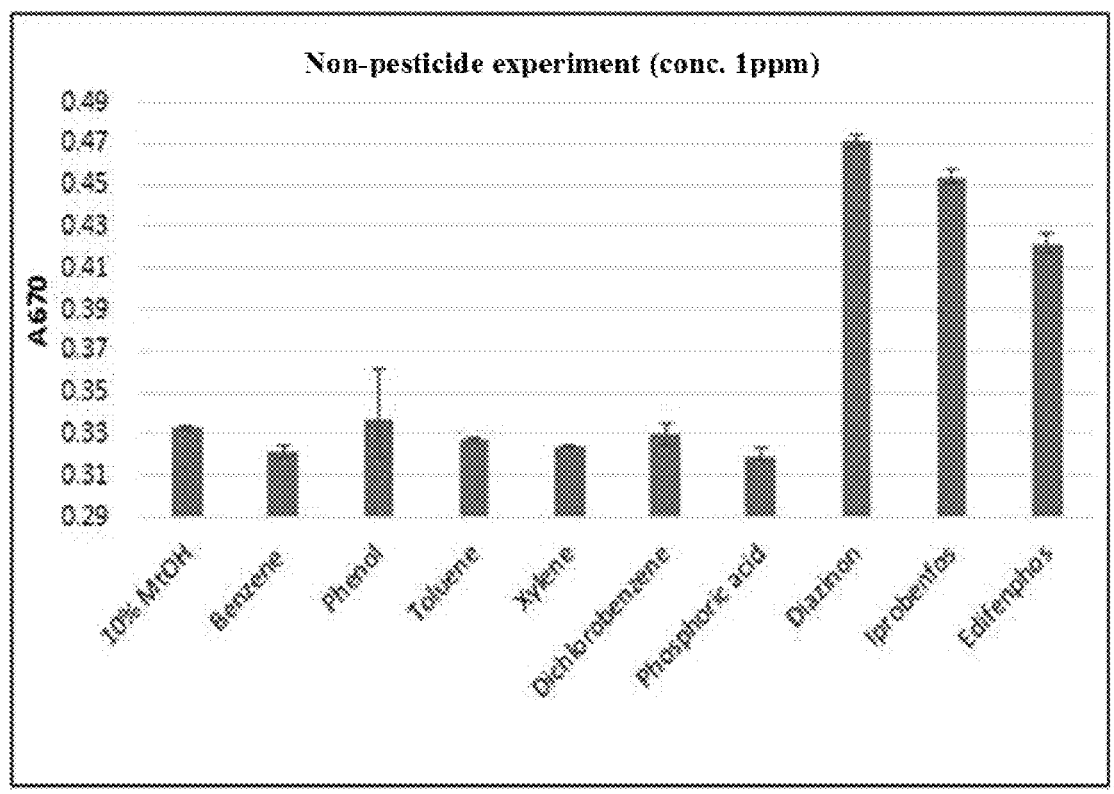
FIG. 15 is a graph showing absorbance measured at 670 nm after adding gold nanoparticles and EGFP to each of non-pesticide compounds and three organophosphorus pesticides.

The absorbance at 670 nm was analyzed. As a result, as shown in FIG. 15, the absorbance was significantly low (0.35 or lower) for benzene, phenol, toluene, xylene, dichlorobenzene, phosphoric acid and the like, which are non-pesticide compounds, and only the absorbance for diazinon, edifenphos and iprobenfos, which are organophosphorus pesticides, was as high as 0.41 or higher, suggesting that the sensor system showed a specific response to the organophosphorus pesticide.

Example 11

Change in Absorbance of Mixture of Organophosphorus Pesticide, Gold Nanoparticle and EGFP as a Function of Time At a wavelength of 670 nm at which the change in absorbance was the greatest, the change in absorbance as a function of time was measured using varying concentrations of an organophosphorus pesticide in order to determine the most suitable reaction time. Absorbance was measured at intervals of 10 minute after an organophosphorus pesticide (0, 0.01, 0.1 and 1.0 ppm of diazinon), gold nanoparticles and EGFP were all added.

Figure 16:
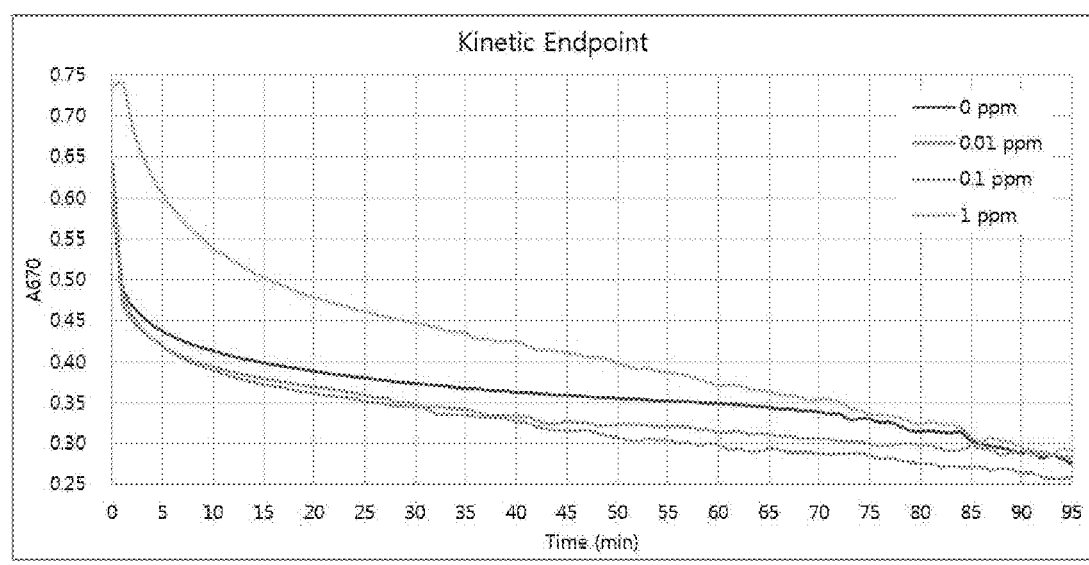
FIG. 16 is a graph showing changes in the absorbance of mixtures of varying concentrations of an organophosphorus pesticide, gold nanoparticles and EGFP, measured at 670 nm as a function of time.

As a result, as shown in FIG. 16, in the initial stage of the reaction, the change in absorbance was great, indicating that the reaction occurred rapidly. Thus, it was found that, when the reaction time was short, the greatest difference in the absorbance value between the concentrations of the pesticide well appeared. It can be seen that absorbance is measured within a very short reaction time, and thus the organophosphorus pesticide can be detected within a short time, and that the reaction occurs continuously over a long period of time.

Example 12

Change in Particle Size of Gold Nanoparticles

Figure 17:
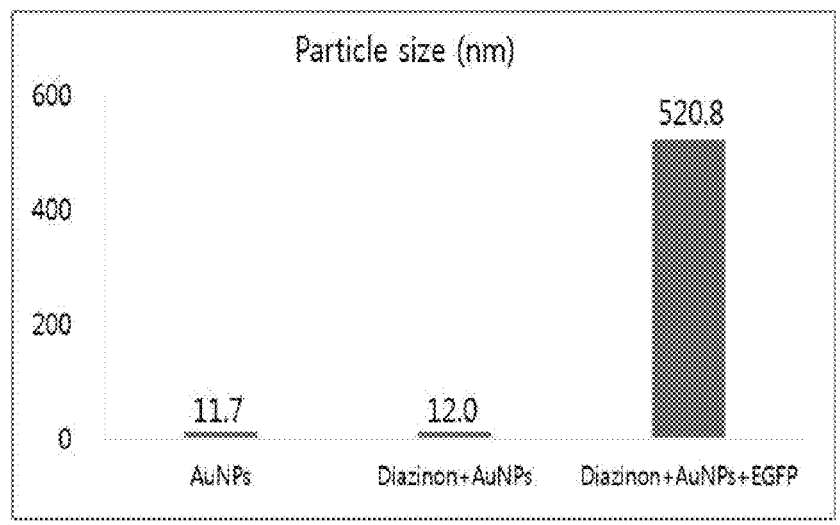
FIG. 17 is a graph showing the change in particle size caused by the aggregation of gold nanoparticles when gold nanoparticles and/or EGFP were added to an organophosphorus pesticide.

An organophosphorus pesticide and an EGFP solution were sequentially added to a gold nanoparticle solution (the concentration and the mixing ratio were the same as described in Example 9-3), the size of the gold nanoparticles following the addition of each of the pesticide and the EGFP solution was measured with a zeta potential particle size analyzer. The size of the gold nanoparticles was 11.7 nm, and when the organophosphorus pesticide was added to the gold nanoparticles, the particle size was 12 nm, which did not greatly change. However, when EGFP was added, the particle size greatly increased to 520.8 nm, suggesting that EGFP greatly influences the aggregation of gold nanoparticles (FIG. 17), as described in Example 9-3.

Example 13

Change in Absorbance of Mixture of Organophosphorus Pesticide, Gold Nanoparticle and EGFP as a Function of pH In order to examine whether the reaction of gold nanoparticles with an organophosphorus pesticide and imidazole is influenced by the pH of the solution, the change in the absorbance at 670 nm with a change in pH was analyzed (the concentration and the mixing ratio were the same as described in Example 9-3).

Figure 18:
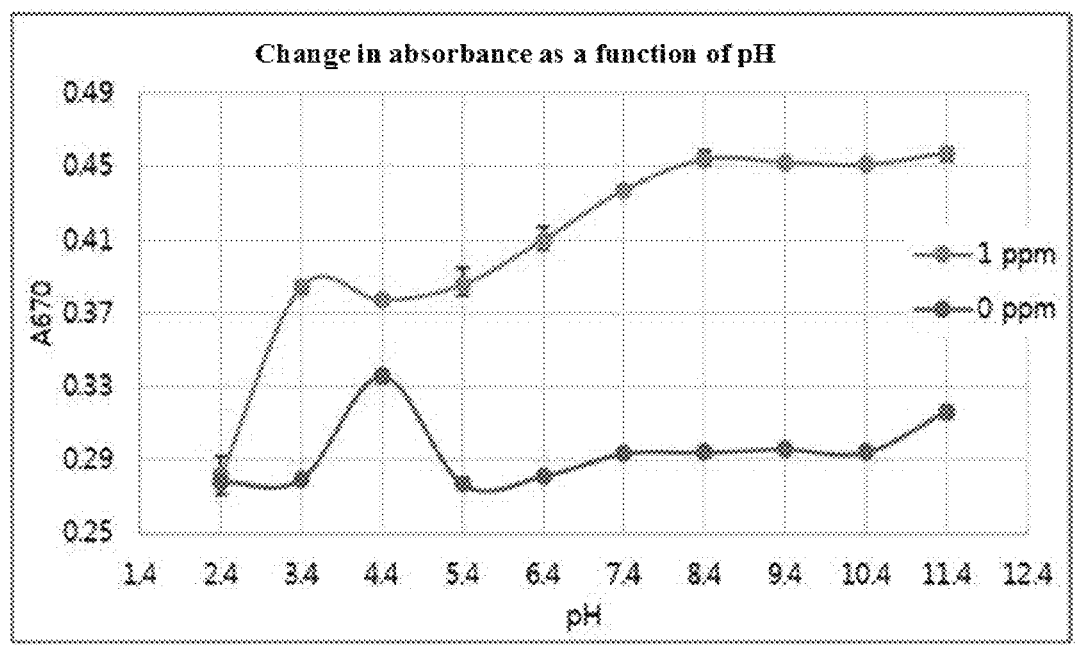
FIG. 18 is a graph showing a change in the absorbance of a mixture of an organophosphorus pesticide, gold nanoparticles and EGFP, measured at 670 nm as a function of pH.

Absorbance was analyzed at a pH ranging from 1.4 to 12.4. As a result, as shown in FIG. 18, when the organophosphorus pesticide was present, the absorbance at 670 nm showed a tendency to increase as the pH increases. Also, the difference in the absorbance between the presence and absence of the organophosphorus pesticide (diazinon) increased as the pH increased. The greatest difference appeared at pH 8.4.

Example 14

Comparison of the Results of Quantifying Organophosphorus Pesticide Using Embodiments of the Present Invention with the Results of Quantifying Organophosphorus Pesticide Using HPLC The results of quantifying the concentration of an organophosphorus pesticide by allowing gold nanoparticles to react with an organophosphorus pesticide and EGFP and then measuring the absorbance were compared with the quantification results obtained by HPLC (high-performance liquid chromatography) that is a general pesticide detection method, in order to demonstrate the accuracy of the inventive method of quantifying an organophosphorus pesticide (the concentrations of the gold nanoparticle solution and the imidazole solution and the mixing ratio were the same as described in Example 9-3).

An organophosphorus pesticide was diluted to concentrations of 0.085 ppm, 0.170 ppm and 0.300 ppm, and then quantitatively analyzed using each of the method of embodiments of the present invention and HPLC. As a result, as can be seen in Table 2 above, the results of the analysis were similar between the method of embodiments of the present invention and HPLC, except for a concentration of 0.085 ppm.

TABLE 2

|  | Samples | | |
| --- | --- | --- | --- |
|  | 1 | 2 | 3 |
| Diazinon conc. Added (ppm) | 0.085 | 0.170 | 0.340 |
| the present method mean ± SD (ppm)* | 0.124 ± 0.015 | 0.156 ± 0.010 | 0.248 ± 0.012 |
| Recovery (%) | 145.9 | 91.8 | 82.7 |
| HPLC mean ± SD (ppm)* | 0.082 ± 0.002 | 0.149 ± 0.002 | 0.263 ± 0.014 |
| Recovery (%) | 96.2 | 87.6 | 87.7 |
| Reliability (%) | 151.6 | 104.7 | 94.3 |

*Mean value of three measurements; SD: standard deviation

The mean recovery obtained when using the quantification method of embodiments of the present invention was 106.8%, which was higher than the mean recovery obtained when using the HPLC quantification method (90.5%). Thus, it can be seen that the pesticide quantification method of embodiments of the present invention is as accurate as HPLC and, at the same time, is more rapid and efficient than HPLC, suggesting that the method of embodiments of the present invention can substitute for the HPLC quantification method.

The system for detecting pesticide residue according to embodiments of the present invention is useful as a biosensor for analyzing pesticide residue in situ, because the optical change of the reagent by the presence of an organophosphorus pesticide is distinct, the detection speed is fast, and the range of detection limits is broad.

Although embodiments of the present invention has been described in detail with reference to the specific features, it will be apparent to those skilled in the art that this description is only for a embodiment and does not limit the scope of the present invention. Thus, the substantial scope of the present invention will be defined by the appended claims and equivalents thereof.

The invention claimed is:

1. A method of detecting an organophosphorus pesticide, the method comprising:
   providing a sample suspected for comprising an organophosphorus pesticide selected from the group consisting of diazinon, edifenphos, iprobenfos, malathion, tebuconazole, parathion, acetamiprid, fenitrothion, and fenthion;
   adding, to the sample, gold nanoparticles and a reagent to provide a mixture, the reagent comprising a compound capable of binding with at least one gold nanoparticle and also capable of reacting with the organophosphorus pesticide such that, if the sample comprises the organophosphorus pesticide, a plurality of molecules of the compound are bonded to one molecule of the organophosphorus pesticide and at least part of the plurality of compound molecules bounded to the one organophosphorus pesticide molecule are bound to a plurality of gold nanoparticles, whereby in the mixture the plurality of gold nanoparticles are aggregated with the one organophosphorus pesticide molecule via the plurality of compound molecules, wherein the compound is at least one selected from the group consisting of imidazole, histidine, pyrozole, histamine, and green fluorescent protein (GFP);
   irradiating light beams to the mixture and measuring light absorbance for determining if aggregations of gold nanoparticles are formed in the mixture; and
   determining a presence of the organophosphorus pesticide in the sample when it is determined that aggregations are formed in the mixture.

2. The method of claim 1, wherein the gold nanoparticles have a diameter of 10-50 nm.

3. The method of claim 1, wherein the gold nanoparticles are added to the sample before adding the reagent.

4. The method of claim 1, wherein the gold nanoparticles are added to provide a concentration of 8-12 nM in the mixture, and the reagent is added to provide the compound's concentration of 0.1-0.4 mM in the mixture.

5. The method of claim 1, wherein the presence of the organophosphorus pesticide represents its concentration of 0.01 ppm or higher in the mixture.

6. The method of claim 1, further comprising adjusting pH of the mixture as 7.4-8.4 prior to irradiating the light beams.

7. A method of determining a concentration of an organophosphorus pesticide, the method comprising:
   determining the presence of the organophosphorus pesticide in accordance with the method of claim 1;
   quantifying a concentration of the organophosphorus pesticide based on the measured absorbance.

8. The method of claim 7, further comprising a pretreatment step of diluting the pesticide-contaminated sample in methanol, ethanol, or an aqueous solution thereof.

9. The method of claim 7, wherein the gold nanoparticles have a diameter of 10-50 nm.

10. The method of claim 7, wherein the gold nanoparticles are added to provide a concentration of 8-12 nM in the mixture, and the reagent is added to provide the compound's concentration of 0.1-0.4 mM in the mixture.

11. The method of claim 7, wherein the concentration of the organophosphorus pesticide is 0.01 ppm or higher.

12. The method of claim 7, further comprising adjusting pH of the mixture as 7.4-8.4 prior to irradiating the light beams.

13. A kit for detecting an organophosphorus pesticide, the kit comprising:
- gold nanoparticles; and
- a reagent comprising a compound capable of binding with at least one gold nanoparticle and also capable of reacting with an organophosphorus pesticide selected from the group consisting of diazinon, edifenphos, iprobenfos, malathion, tebuconazole, parathion, acetamiprid, fenitrothion, and fenthion,
- wherein when mixed with a sample suspected for comprising the organophosphorus pesticide to form a mixture comprising the gold nanoparticles, the reagent and the sample and if the sample comprises the organophosphorus pesticide, a plurality of molecules of the compound are bonded to one molecule of the organophosphorus pesticide and at least part of the plurality of compound molecules bounded to the one organophosphorus pesticide molecule are bound to a plurality of gold nanoparticles, whereby in the mixture the plurality of gold nanoparticles are aggregated with the one organophosphorus pesticide molecule via the plurality of compound molecules.

* * * * *